United States Patent [19]
Subramaniam et al.

[11] Patent Number: 5,907,075
[45] Date of Patent: May 25, 1999

[54] SOLID ACID SUPERCRITICAL ALKYLATION REACTIONS USING CARBON DIOXIDE AND/OR OTHER CO-SOLVENTS

[75] Inventors: Bala Subramaniam; Michael C. Clark, both of Lawrence, Kans.

[73] Assignee: The University of Kansas, Lawrence, Kans.

[21] Appl. No.: 08/872,865

[22] Filed: Jun. 11, 1997

[51] Int. Cl.$^6$ .................................. C07C 2/56; C07C 2/58
[52] U.S. Cl. ........................... 585/721; 585/709; 585/711
[58] Field of Search ..................................... 585/709, 711, 585/721

[56] References Cited

U.S. PATENT DOCUMENTS

| | | | |
|---|---|---|---|
| 5,304,698 | 4/1994 | Husain | 585/722 |
| 5,639,930 | 6/1997 | Penick | 585/709 |

OTHER PUBLICATIONS

Nakamura et al.; Supercritical Phase Isobutane/Olefin Alkylation on Solid Acids;*Am. Chem. Soc.*, Div. pet. Chem., preprints (1996).

Fan et al.; Supercritical–Phase Alkylation Reaction on Solid Acid Catalysts:Mechanistic Study and Catalyst Development; *Ind. Eng. Chem. Res.* 36:1458–1463 (1997).

*Primary Examiner*—Glenn A. Caldarola
*Assistant Examiner*—In Suk Bullock
*Attorney, Agent, or Firm*—Hovey, Wiilaims, Timmons & Collins

[57] ABSTRACT

Improved isoparaffin-olefin alkylation solid catalyst processes are provided which are characterized by low coke laydown and catalyst deactivation rates and production of valuable branched chain, high octane number alkylates. The processes of the invention involve providing a starting reactant mixture comprising an isoparaffin, an olefin and a co-solvent or diluent (carbon dioxide in molar excess, methane, hydrogen or mixtures thereof), and contacting the reactant mixture with an alkylation catalyst at near-critical or preferably supercritical conditions for the reaction mixture. The carbon dioxide serves as a co-solvent and reduces the critical temperature ($T_c$) of the reaction mixture, thereby allowing lower reaction temperatures. The isoparaffin and olefin reactants are preferably pretreated to minimize moisture, peroxide and oxygenate impurities therein.

33 Claims, 2 Drawing Sheets

SOLID ACID SUPERCRITICAL ALKYLATION REACTIONS USING CARBON DIOXIDE AND/OR OTHER CO-SOLVENTS

BACKGROUND OF THE INVENTION

1. Field of the Invention

The present invention is broadly concerned with improved isoparaffin-olefin alkylation processes used for the conversion of low carbon number paraffins and olefins into valuable, high octane number compounds useful in gasolines. More particularly, the invention pertains to such alkylation processes wherein the problem of coke laydown and catalyst deactivation is minimized and the production of high octane number alkylates is enhanced by carrying out the alkylation reaction at near-critical or supercritical conditions and by using a co-solvent or diluent such as carbon dioxide in a molar excess.

2. Description of the Prior Art

Alkylation processes are used industrially to convert light refinery gases such as $C_4$–$C_5$ isoparaffins into more valuable branched chain gasoline-range $C_7$–$C_9$ alkylate compounds. Particularly valuable alkylates are trimethylpentanes (TMPs) and 2,2-dimethylbutane (neohexane) which are used as high-octane blending components for aviation and civilian gasolines. It is estimated that about 13% of the U.S. gasoline pool is made up of alkylates.

Conventional alkylation processes utilize HF or $H_2SO_4$. These acidic processes are undesirable for a number of reasons including environmental and transportation hazards, and the difficulty of economical acid disposal or regeneration. Alkylation processes are also known where the isoparaffin and olefin reactants contact a zeolite, sulfated zirconia, wide-pore MCM-type or other solid alkylation catalysts at elevated temperature and pressure reaction conditions.

A significant problem with solid-catalyzed alkylation processes is the tendency for the catalysts to rapidly deactivate by virtue of coke laydown on the catalyst which tends to plug the catalyst pores. This problem is compounded in that most solid alkylation catalysts cannot be regenerated without causing irreversible degradation of the catalysts. Certain reactor operating strategies have been proposed to mitigate the problem of coke laydown, such as the use of a slurry reactor or supercritical operation. However, these efforts have not been truly successful; for example, at the high temperatures required to achieve supercritical reaction conditions when not using a co-solvent or diluent such as carbon dioxide, undesirable side reactions such as oligomerization and cracking are favored. As a consequence, while catalytic alkylation processes have shown promise, a number of intractable problems exist which limit the practical utility thereof.

SUMMARY OF THE INVENTION

The present invention overcomes the problems outlined above and provides improved alkylation processes which ameliorate catalyst deactivation stemming from coke laydown and which give enhanced yield of preferred branched chain, high octane number alkylates. Broadly speaking, the processes of the invention involve providing a reaction mixture comprising an isoparaffin, an olefin and a molar excess of an inert co-solvent or diluent such as carbon dioxide, methane or hydrogen (relative to the moles of isoparaffin and olefin); the co-solvent or diluent has a critical temperature that is lower than the critical temperatures of both the isoparaffin and olefin starting reactants. This reactant mixture is contacted with a solid porous alkylation catalyst to produce a reaction mixture containing alkylate, and the critical temperature ($T_c$) of the reaction mixture is significantly lowered owing to the presence of excess inert co-solvent(s). The contacting step is generally carried out in a reactor at near-critical or supercritical conditions for the reaction mixture, typically at temperatures of from about 0.9–1.3 $T_c$ of the reaction mixture and a pressure of from about 300–3500 psi. In preferred forms, the contacting step is carried out at supercritical conditions for the reaction mixture (1.01–1.3 $T_c$ of the reaction mixture, preferably 1.01–1.2 $T_c$), typically from about –50–200° C., and most preferably 5–100° C., with the pressure being in excess of the critical pressure ($P_c$) for the reaction mixture.

The alkylation processes of the invention can be carried out using a variety of reactants and operating conditions. For example, the isoparaffin and olefin reactants can be selected from the $C_4$–$C_{10}$ isoparaffins and olefins, while the $CO_2$:(isoparaffin+olefin) mole ratio can be within the range of from about 5:1–300:1. Any suitable alkylation catalyst can be used, such as a zeolite, sulfated zirconia or other solid catalysts which favor alkylate formation. The catalyst surface area can generally range from about 5–1000 $m^2/g$ while the catalyst pore volume can range from about 0.01–0.5 cc/g. The fluid density of the reaction mixture generally ranges from about 0.05–0.65, but can be greater if desired; it will be understood that this density is significantly affected by the reaction pressure. It is particularly preferred that the isoparaffin and olefin reactants be pretreated to remove moisture, peroxide and oxygenate impurities or other free radical producing species which catalyze oligomer formation in the bulk fluid phase, which have been found to adversely affect catalyst performance. As used herein, oxygenates refer to free-radical or free-radical providing oxygenate compounds. The total content of peroxides in the isoparaffin and olefin reactants should be no more than about 200 ppm, while the oxygenate concentration should be no more than about 200 ppm.

It has been found that the use of a co-solvent or diluent such as $CO_2$ allows lower temperature alkylation resulting in reduced catalyst coking rates and increased production of valuable TMPs. Moreover, $CO_2$ is an inexpensive component which is environmentally friendly and fully recyclable. In addition, operation at supercritical reaction conditions relative to the alkylate reaction mixture where $CO_2$ or other suitable diluent is used as a co-solvent gives an optimum combination of gas-like transport properties and liquid-like densities. This serves to extract coke precursors in situ from the solid porous catalysts. Consequently, catalyst deactivation rates are minimized, and the rates of the desired alkylation reactions to give a narrower alkylate spectrum are maximized.

DETAILED DESCRIPTION OF THE PREFERRED EMBODIMENT

The following Example illustrates various alkylation reactions carried out using liquid, gas, near-critical and supercritical reaction conditions, with and without carbon dioxide as a co-solvent. It is to be understood that the example is provided by way of demonstration only and nothing therein should be taken as a limitation upon the overall scope of the invention.

EXAMPLE

In these series of alkylation tests, a conventional plug flow alkylation reactor was employed for the alkylation reaction between isobutane ($T_c$=135° C., $P_c$=529 psi) with butene ($T_c$=146° C., $P_c$=583 psi) and in certain cases using an excess of $CO_2$ ($T_c$=31° C., $P_c$=1071 psi), using two separate alkylation catalysts. In the first series, 5 g of a USHY zeolite catalyst was employed having a Si:Al ratio of 2.8, a surface area of 560 $m^2$/g, a pore volume of 0.33 cc/g; the catalyst was pretreated at 450° C. for 3 hrs. In the second series, 10 g of sulfated zirconium hydroxide catalyst was employed, having 4% $SO_4$, a surface area of 100 $m^2$/g, and a pore volume of 0.07 cc/g; this catalyst was pretreated at 600° C. for 1 hr. to transform it into the oxide form. The butane and butene reactants were pretreated by contact with activated alumina to remove peroxides. For the runs using the zirconia catalysts, the feed was also treated with sodium sulfate to remove moisture traces and oxygenates.

The reaction operating conditions were: temperature, 50–176° C.; pressure 500–2250 psi; olefin WHSV (weight hourly space velocity), 0.25 $hr^{-1}$; isoparaffin:olefin molar ratio, 9:1; $CO_2$:(isoparaffin:olefin) molar ratio, 90:9:1 (95° C.), 180:9:1 (50° C.). The extent of butene conversion was monitored along with the ratio of the preferred trimethylpentanes versus $C_5$ and above alkylates.

Figure 1:
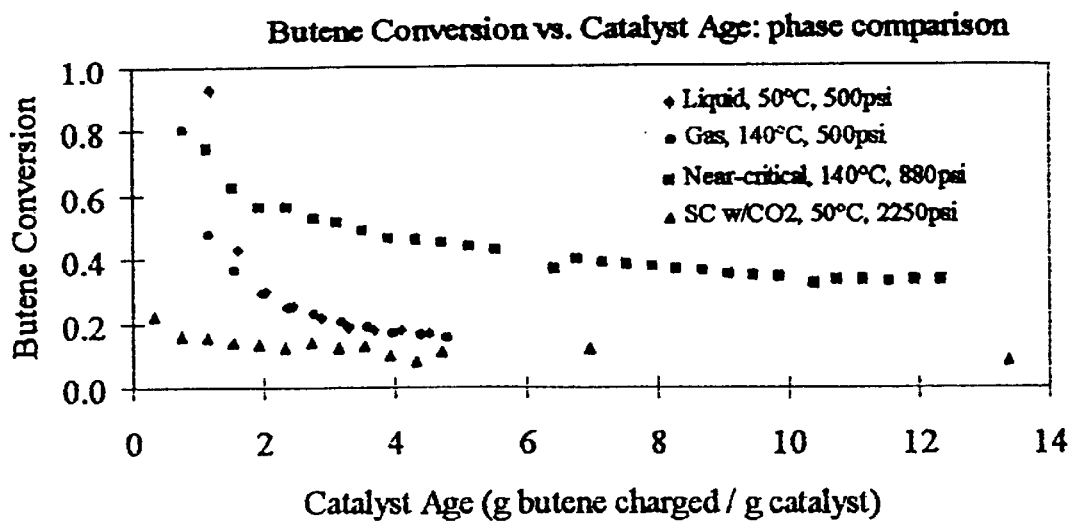
FIG. 1 is a graph of butene conversion versus USHY catalyst age in a series of phase comparison alkylation (isoparaffin-butene) reactions, using a zeolite catalyst.
Figure 2:
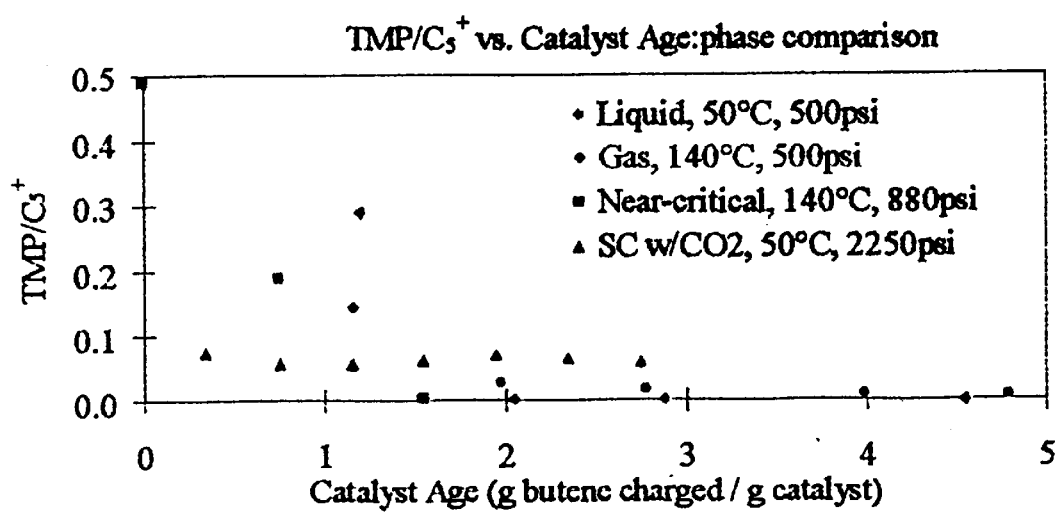
FIG. 2 is a graph of total trimethlypentanes/$C_{5+}$ versus USHY catalyst age for the phase comparison alkylation reactions of FIG. 1.
Figure 3:
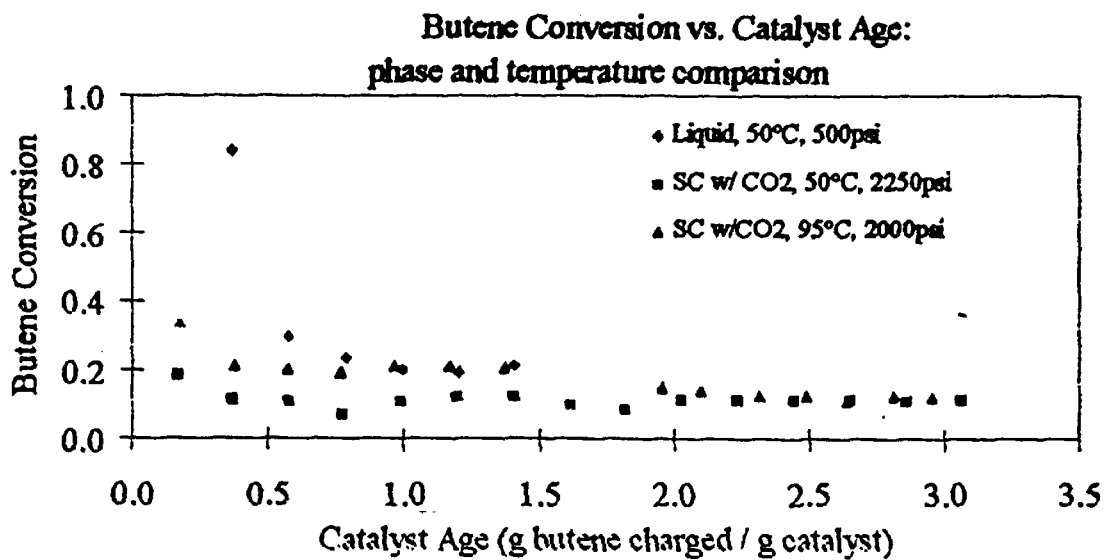
FIG. 3 is a graph of butene conversion versus catalyst age in a series of phase comparison alkylation (isoparaffin-butene) reactions, using a sulfated zirconia catalyst.
Figure 4:
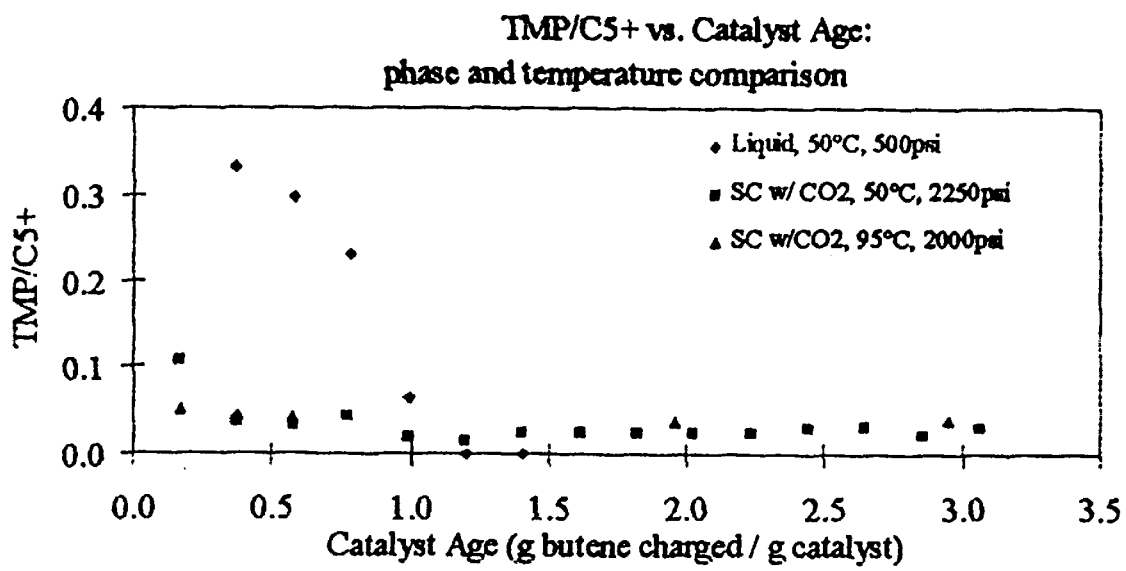
FIG. 4 is a graph of trimethlypentane/$C_{5+}$ versus sulfated zirconia catalyst age for the phase comparison alkylation reactions of FIG. 3.

FIGS. 1 and 2 illustrate the results obtained (i.e., butene conversion and TMP/$C_{5+}$) using the zeolite catalyst for four different reaction phases, namely liquid phase at 50° C. and 500 psi, gas phase at 140° C., 500 psi, near-critical phase at 140° C., 880 psi, and supercritical phase with $CO_2$ as co-solvent at 50° C., 2250 psi. FIGS. 3 and 4 provide similar data for the sulfated zirconia catalyst.

The results of these tests demonstrated that butene conversion reached a steady state in all reaction phases, using both the zeolite and zirconia catalysts. However, gas phase high temperature operation resulted in cracked products ($C_5$–$C_7$) which are undesirable owing to their low octane number. Moreover, the data of FIGS. 2 and 4 confirmed that extended activity for TMP alkylate production is obtained only during supercritical operation with $CO_2$ as a co-solvent. Further, analysis of the catalyst samples after completion of the reactions established that supercritical phase operation with $CO_2$ as a co-solvent gave more catalyst surface area and pore volume, as compared with the other tests. The following table 1 sets forth a comparison of fresh and after-reaction catalyst properties observed in these tests.

TABLE 1

| Catalyst | Condition | I:O:$CO_2$ molar ratio | Surface Area ($m^2$)/g | Pore Volume ($cm^3$/g) | Observed Color |
|---|---|---|---|---|---|
| USY | Fresh | — | 560 | 0.33 | white |
| USY | Liquid phase, 50° C., 500 psi | 9:1:0 | 350 | 0.22 | yellow-beige |
| USY | Gas phase, 140° C., 500 psi | 9:1:0 | 130 | 0.09 | brown |
| USY | Near-critical, 140° C., 1000 psi | 9:1:0 | 190 | 0.13 | brown |
| USY | Supercritical, 50° C., 2250 psi | 9:1:90 | 430 | 0.25 | off-white |
| USY | Supercritical, 95° C., 2250 psi | 9:1:180 | 420 | 0.25 | beige |
| SZ | Fresh | — | 100 | 0.07 | white |
| SZ | Liquid phase, 50° C., 500 psi | 9:1:9 | 10 | 0.01 | yellow |
| SZ | Supercritical, 50° C., 2250 psi | 9:1:90 | 45 | 0.06 | off-white |
| SZ | Supercritical, 95° C., 2250 psi | 9:1:180 | 35 | 0.03 | brown |

I = iso-butane
O = butene
$CO_2$ = carbon dioxide
USY = ultrastable "Y" zeolite
SZ = sulfated zirconia
USY runs: feed pretreatment with activated alumina unless otherwise indicated
SZ runs: feed pretreated with activated alumina and sodium sulfate It will be appreciated that the alkylation reactions of the invention can be carried out using a number of different alkylation catalysts and reaction conditions. The following Table 2 summarizes these variables in terms of approximate broad and preferred ranges.

TABLE 2

| Reaction Parameter | Broad Range | Preferred Range |
|---|---|---|
| Isoparaffin Type (carbon number) | $C_4$–$C_{10}$ | $C_4$–$C_5$ |
| Olefin Type (carbon number) | $C_2$–$C_{10}$ | $C_2$–$C_6$ |
| Co-Solvent/Diluent Type | $CO_2$, $CH_4$ and/or $H_2$ | $CO_2$ |
| Reaction Temperature (relative to $T_c$ of reaction mixture) | 0.9–1.3 $T_c$ | 1.01–1.2 $T_c$ |
| $T_c$ of Reaction Mixture (° C.) | −50–200 | 5–100 |
| Reaction Pressure (psi) | 14–3500 | 500–3000 |
| Isoparaffin:Olefin mole ratio | 4:1–20:1 | 7:1–12:1 |
| Co-Solvent/Diluent:Isoparaffin mole ratio | 0.01:1–50:1 | 2:1–20:1 |
| $CO_2$:Isoparaffin mole ratio | 5:1–25:1 | 10:1–20:1 |
| Co-Solvent/Diluent:Olefin mole ratio | 1:1–300:1 | 20:1–200:1 |
| $CO_2$:Olefin mole ratio | 50:1–300:1 | 70:1–200:1 |
| Co-Solvent/Diluent:Isoparaffin + Olefin mole ratio | 0.01:1–325:1 | 1:1–200:1 |
| $CO_2$:(Isoparaffin + Olefin) mole ratio | 2:1–300:1 | 10:1–80:1 |
| Reactant Peroxide Content (ppm) | up to 200 | up to 50 |
| Reactant Oxygenate Content (ppm) | up to 200 | up to 50 |
| Reactant Moisture Content (ppm) | up to 100 | up to 50 |
| Catalyst Surface Area (BET, $m^2$/g) | 5–1000 | 10–600 |
| Catalyst Pore Volume (cc/g) | 0.01–0.5 | 0.05–0.4 |
| Reaction Mixture Fluid Density (g/cc) | 0.05–0.65 | 0.2–0.5 |

We claim:

1. An alkylation process comprising the steps of:
   providing a reactant mixture comprising an isoparaffin, an olefin and a molar excess of an inert co-solvent or diluent; and
   contacting said reactant mixture with a solid alkylation catalyst to produce a reaction mixture containing alkylate, said contacting step being carried out at supercritical conditions for the reaction mixture, and said reaction mixture having a fluid density of from about 0.05–0.65 g/cc.

2. The process of claim 1, said isoparaffin being selected from the $C_4$–$C_{10}$ isoparaffins.

3. The process of claim 1, said olefin being selected from the $C_2$–$C_{10}$ olefins.

4. The process of claim 1, said reactant mixture comprising a plurality of feed reactants, said co-solvent or diluent having a critical temperature less than each of the feed reactants.

5. The process of claim 1, said co-solvent or diluent being selected from the group consisting of carbon dioxide, methane, hydrogen and mixtures thereof.

6. The process of claim 1, said contacting step being carried out at supercritical conditions for said reaction mixture.

7. The process of claim 1, said temperature being from about 0.9–1.3 $T_c$ of the reaction mixture.

8. The process of claim 1, said pressure being from about 500–3000 psi.

9. The process of claim 1, said catalyst having a surface area from about 5–1000 $m^2$/g.

10. The process of claim 1, said catalyst having a pore volume of from about 0.01–0.5 cc/g.

11. The process of claim 1, the co-solvent/diluent:isoparaffin mole ratio being from about 0.01:1 to 501.

12. The process of claim 1, the co-solvent/diluent:olefin mole ratio being from about 1:1 to 300:1.

13. The process of claim 1, said alkylation catalyst being selected from the group consisting of the zeolite and sulfated zirconia catalysts.

14. The process of claim 1, said isoparaffin being selected from the $C_4$–$C_5$ isoparaffins and said olefin being selected from the $C_3$–$C_6$ olefins.

15. The process of claim 14, said olefin being butene.

16. The process of claim 1, said reaction temperature being from about 5–100° C.

17. The process of claim 1, said reactant mixture having a peroxide content of up to 200 ppm.

18. The process of claim 1, said reactant mixture having a moisture content of up to about 100 ppm.

19. The process of claim 1, said contacting step being carried out at a temperature of from about –50 to 200° C. and a pressure of from about 14–3500 psi.

20. An alkylation process comprising the steps of:
    providing a reactant mixture comprising an isoparaffin, an olefin and an inert co-solvent or diluent; and
    contacting said reactant mixture with an alkylation catalyst to produce a reaction mixture containing alkylate, said contacting step being carried out at supercritical conditions for the reaction mixture, and said reaction mixture having a fluid density of from about 0.05–0.65 g/cc.

21. The process of claim 20, said isoparaffin being selected from the $C_4$–$C_{10}$ isoparaffins.

22. The process of claim 20, said olefin being selected from the $C_2$–$C_{10}$ olefins.

23. The process of claim 20, said co-solvent or diluent being selected from the group consisting of carbon dioxide, methane, hydrogen and mixtures thereof.

24. The process of claim 20, said contacting step being carried out at a temperature of from about 1.01–1.3 $T_c$ of the reaction mixture.

25. The process of claim 20, said contacting step being carried out at a pressure of from about 500–3000 psi.

26. The process of claim 20, said catalyst having a surface area from about 5–1000 $m^2$/g.

27. The process of claim 20, said catalyst having a pore volume of from about 0.01–0.5 cc/g.

28. The process of claim 20, the co-solvent/diluent:isoparaffin mole ratio being from about 0.01:1 to 50.

29. The process of claim 20, the co-solvent/diluent:olefin mole ratio being from about 1:1 to 300:1.

30. The process of claim 20, said alkylation catalyst being selected from the group consisting of the zeolite and sulfated zirconia catalysts.

31. The process of claim 20, said isoparaffin being selected from the $C_4$–$C_5$ isoparaffins and said olefin being selected from the $C_3$–$C_6$ olefins.

32. The process of claim 20, said reaction temperature being from about –50–200° C.

33. An alkylation process comprising the steps of:
    providing a reactant mixture comprising an isoparaffin, an olefin and an inert co-solvent or diluent, said co-solvent or diluent having a critical temperature lower than the individual critical temperatures of said isoparaffin and of said olefin; and
    contacting said reactant mixture with an alkylation catalyst to produce a reaction mixture containing alkylate, said contacting step being carried out at supercritical conditions for the reaction mixture.

* * * * *